United States Patent [19]

Wayne et al.

[11] Patent Number: 5,137,020
[45] Date of Patent: Aug. 11, 1992

[54] BATTERY IMPEDANCE MEASUREMENT APPARATUS

[75] Inventors: David A. Wayne, Scottsdale; Tho Huyhn, Mesa, both of Ariz.; Jeff Ireland, Brooklyn Park, Minn.

[73] Assignee: Medtronic, Inc., Minneapolis, Minn.

[21] Appl. No.: 619,519

[22] Filed: Nov. 29, 1990

[51] Int. Cl.⁵ .............................................. A61N 1/08
[52] U.S. Cl. ........................ 128/419 PS; 128/419 PT
[58] Field of Search .................... 128/419 PT, 419 PS

[56] References Cited

U.S. PATENT DOCUMENTS

| | | | |
|---|---|---|---|
| 4,231,027 | 10/1980 | Mann et al. | 340/636 |
| 4,259,639 | 3/1981 | Renirie | 324/430 |
| 4,324,251 | 4/1982 | Mann | 128/419 PT |

Primary Examiner—William E. Kamm
Assistant Examiner—Scott M. Getzow
Attorney, Agent, or Firm—Harold R. Patton; John A. Rissman; John L. Rooney

[57] ABSTRACT

A battery impedance measurement apparatus for battery powered implantable medical apparatus in which current source means and reference impedance means are selectively connected across the battery after it has been isolated from the medical apparatus, and the resulting currents of interest are digitized to provide a factor directly related to the value of the internal impedance of the battery. The digitized value may be telemetered out of the implanted medical apparatus to enable critical decisions to be made based on the remaining life of the implanted battery. The same measurement apparatus can be used to form an accurate end-of-life signal.

18 Claims, 3 Drawing Sheets

BATTERY IMPEDANCE MEASUREMENT APPARATUS

BACKGROUND OF THE INVENTION

1. Field of the Invention

The present invention is related to electrical medical apparatus, and more particularly, to a battery impedance measurement device for use in an implanted battery powered medical apparatus with telemetering capabilities.

2. Description of the Prior Art

It is well own in the field of implantable medical apparatus that one of the most critical decisions to be made by the medical caretaker is when to replace the implanted battery. Many systems for determining an end-of-life (EOL) signal have been developed and disclosed which alleviate one aspect of the problem; that is, the battery must be replaced as soon as reasonably possible after the EOL signal. However, with the advent of improved batteries which provide many years of life to the implanted medical apparatus, the need has arisen to have accurate information on just how much longer the battery will last under its normal loading, as opposed to a simple EOL signal.

Various prior art circuits have been developed to provide the desired information, such as those disclosed, by way of example, in U.S. Pat. Nos. 4,231,027; 4,259,639; and 4,324,251. While part of the teachings of this prior art is the well recognized fact that the remaining battery life is directly related to the existing internal battery impedance, none of these teachings disclose a circuit for measuring the battery impedance with the accuracy and manufacturing conveniences of the present invention.

SUMMARY OF THE INVENTION

It is the primary object of this invention to provide an improved battery impedance measurement circuit that is especially useful in the environment of an implantable battery powered medical device that has a telemetering capability. Generally, the invention provides current source means and reference impedance means which are selectively connected to the battery after it has been isolated from the medical apparatus. The resulting currents are utilized to provide a factor indicative of the battery impedance. The invention provides the desired information about remaining battery life through a digitized, telemetered signal. In one preferred embodiment, a first current is developed by connecting a first digital-to-analog current generator and a known reference resistor in circuit with the isolated battery; a second current is developed by connecting another digital-to-analog current generator in circuit with the isolated battery. The two currents are presented to the input of a comparator, and the resulting comparator output is sent through a successive approximation register to selectively vary the output of the first digital-to-analog current generator. Because the battery impedance is mathematically related to the ratio of the first and second currents times the value of the reference impedance, its value can be found by varying either the output of the first current generator, as described, or varying the value of the reference impedance.

In another preferred embodiment, the first current generator is varied by the output of the successive approximation register to provide an automatic zeroing at the input of the comparator. The second current is then provided to the input of the comparator to be compared to a reference circuit including a reference impedance. The second current generator is stepped up by the output of the successive approximation generator to achieve the necessary comparison level, and because the value of the second current is mathematically related to the battery impedance, it can be shown that dividing the digitized value of the second current into the known reference impedance will yield the desired value of the serial battery impedance.

Both of the above described embodiments provide means for storing the digitized information and then telemetering it from the implanted apparatus to an external device.

It is a further object of this invention to provide an accurate end-of-life signal from battery powered implantable medical apparatus. This object is achieved through the use of the same circuitry described above as the preferred embodiments, and the digitized telemetered signal is used to set off some form of EOL alarm when the value of the internal battery impedance has reached a predetermined level.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
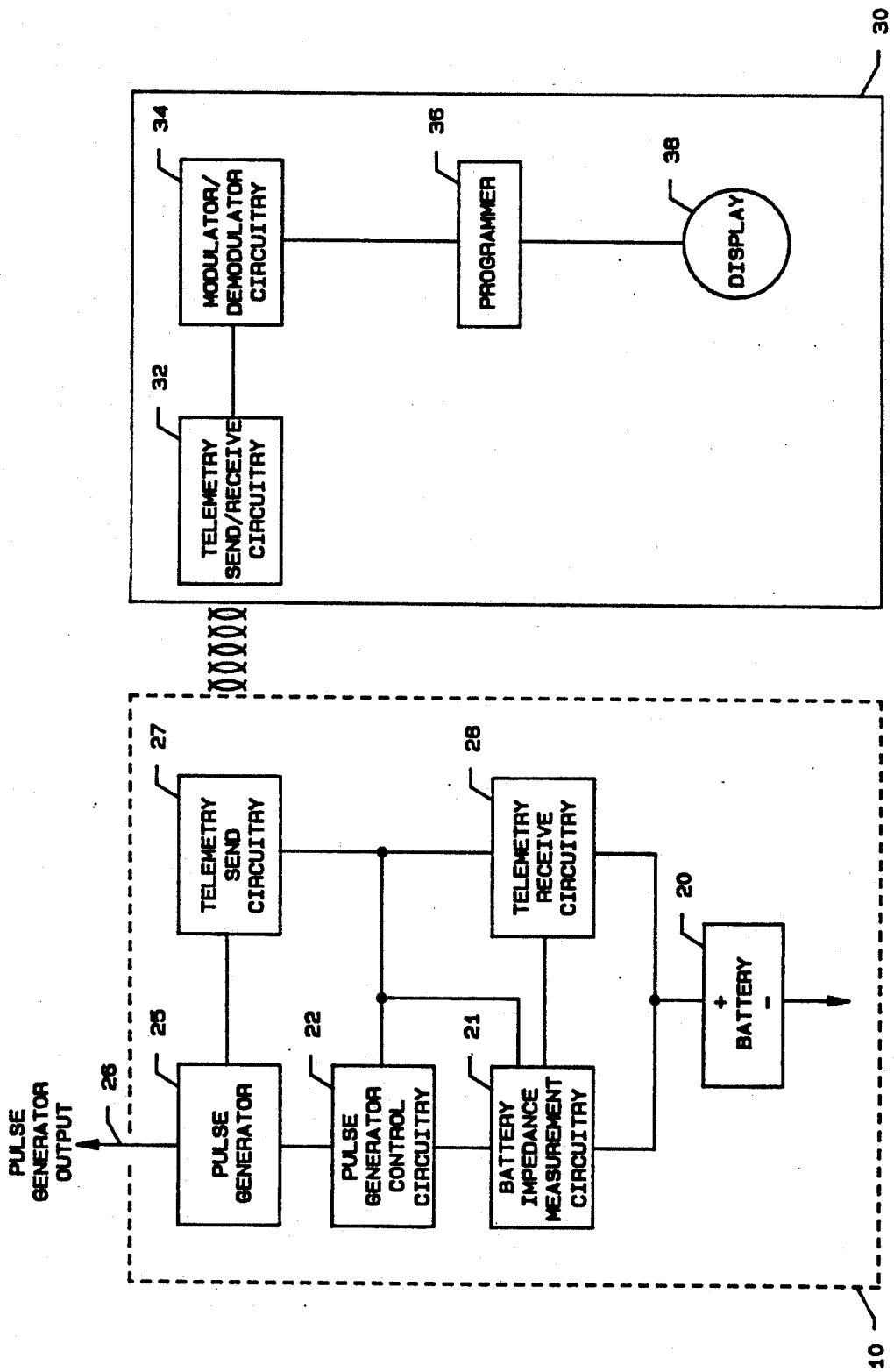
FIG. 1 is a block diagram of a battery operated, body implantable medical apparatus for providing electrical pulses to a selected portion of the body, and includes a telemeter station designed to communicate with the implanted apparatus from a point external to the body.

FIG. 1 is a block diagram shown here as representative of the type of implantable medical apparatus for which the present invention is especially advantageous. A battery operated, body implantable medical device 10 is shown generally within dotted lines. The dotted lines being indicative of the implantation of medical device 10 within a body. Medical device 10 may be any one of a number of implantable medical/electrical circuits, and is shown here as a pulse generator, for example, of the type which may be used in a cardiac pacemaker, a device well known to those of skill in the art.

Medical device 10 is shown as having telemetry capability for communicating with a telemetry controller 30. The use of telemetry with implantable medical apparatus for controlling and reading signals from and to the implanted apparatus is now so well known in the art that no further general explanation is needed; see for example, U.S. Pat. No. 4,231,027 cited earlier in this specification.

Referring further to FIG. 1, implanted medical device 10 is shown as including a battery 20 connected to provide power to the other elements of implanted medical device 10. Medical device 10 also includes battery impedance measurement circuitry 21, which contains the present invention, pulse generator control circuitry 22, pulse generator 25 having an output 26, telemetry send circuitry 27 and telemetry receive circuitry 28. All the elements of medical device 10 are well known to those of skill in the art, with the exception of battery impedance measurement circuitry 21, the subject of this invention, which will be more fully described in the discussions of FIGS. 2 and 3 below.

Telemetry controller 30 includes telemetry send and receive circuitry 32, modulate/demodulate circuitry 34, programmer 36 and display means 38.

As is well known, programmer 36 can be controlled by an operator to send a plurality of signals to medical device 10 that comprise, for example, a set of parameters for the output of pulse generator 25. The signals from programmer 36 are modulated by circuitry 34 and telemetered by telemetry send and receive circuitry 32 to medical device 10. Telemetry receive circuitry 28 will receive and demodulate the signals and present them to pulse generator control circuitry 22 which will use the signals to set the parameters for pulse generator 25. Telemetry send circuitry 27 of medical device 10 may be used, for example, to review the output of pulse generator 25 and modulate and send the information to telemetry send and receive circuitry 32 of telemetry controller 30. The information is then demodulated in modulate/demodulate circuitry 34 and presented to programmer 36, and thence to display means 38 for review by the operator.

When the apparatus of this invention forms a part of medical device 10, as shown by battery impedance measurement circuitry 21, programmer 36 may be selectively actuated to send a signal through the telemetry path described above to activate battery impedance measurement circuitry 21. When this signal is received, battery impedance measurement circuitry 21 will measure the internal impedance of battery 20 at that point in time, in a manner fully described below in the discussions of the preferred embodiments of this invention. This measurement is extremely valuable as the internal impedance of implanted battery 20 is directly related to its remaining lifetime under normal operation of medical device 10. When the desired measurement is completed, battery impedance measurement circuitry 21 will provide a signal containing the measurement value through the telemetry path to telemetry controller 30 where it will eventually be received by programmer 36 and displayed on display means 38.

Figure 2:
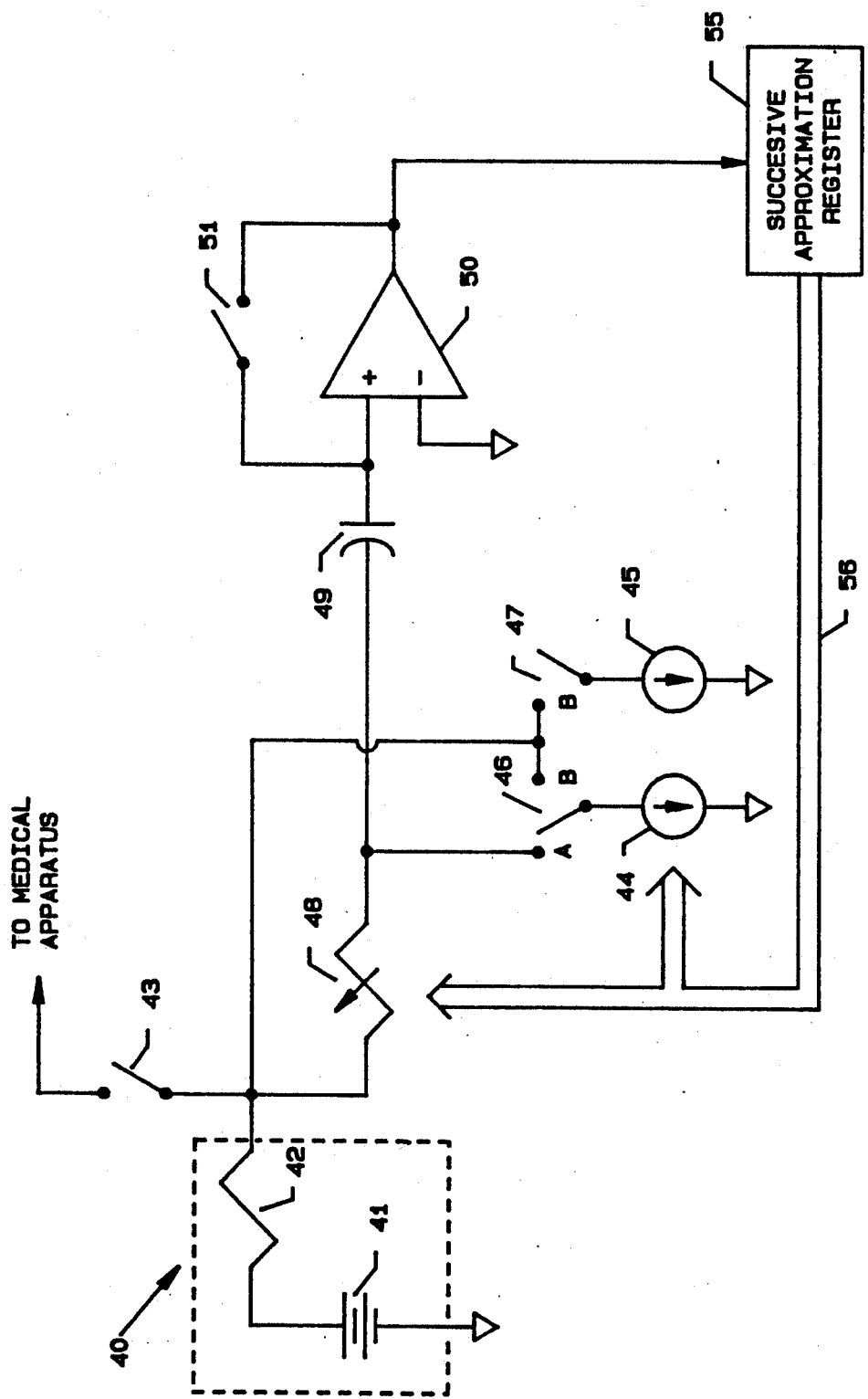
FIG. 2 is a schematic drawing of a preferred embodiment of the battery impedance measurement circuit of this invention; and, FIG. 3 is a schematic drawing of another preferred embodiment of this invention.

FIG. 2 is a schematic diagram of a first embodiment of this invention showing a battery 40 having an internal voltage $V_b$, shown as element 41, and an internal impedance, $R_b$, shown as element 42. A switch 43 is provided for isolating battery 40 from the implanted medical apparatus it powers for the impedance measurement period. An adjustable reference impedance 48, having a value $R_r$, is shown connected between battery 40 and the positive input terminal of a comparator 50, through a capacitor 49.

A first current generator 44 is shown connected between a switch 46 and ground. Switch 46 has terminals A and B. When terminal A of switch 46 is contacted, first current generator 44 will be connected through adjustable reference impedance 48 across battery 40 to provide a first driven input, $I_r$. A switch 51 having a terminal A is connected between the positive input terminal of comparator 50 and the output terminal of comparator 50. Thus, when switch 46 contacts it terminal A, switch 51 will also contact its terminal A, such that the voltage, $V_r$, generated by current $I_r$ will be stored in capacitor 49.

A second current generator 45 is shown connected between a switch 47 and ground. Switch 47 has a terminal B. When switch 47 contacts terminal B, second current generator 45 will be connected across battery 40 to provide a second driven current, $I_b$. At the same time, switch 46 contacts its terminal B to also be connected across battery 40 and to again provide $I_r$. In this preferred embodiment, generators 44 and 45 are digital-to-analog converters, a device well known to those of skill in the art, and generators 44 and 45 may in fact be separate parts of a single digital-to-analog converter.

After both $I_r$ and $I_b$ have been generated, comparator 50 can decide whether $(I_r+I_b) R_b$ is greater or less than $I_r(R_b+R_r)$. Using this information, a value of $I_r$ can be found such that:

$$(I_r+I_b) R_b \gtreqless I_r(R_b+R_r)$$

or $$R_b = (I_r/I_b) R_r$$

To accomplish the desired end, the output of comparator 50 is connected to a successive approximation register 55 which in turn provides an output signal on a data bus 56 that is connected to first current generator 44 and thus also control current $I_r$. Through the use of successive approximation register 55, the ratio $(I_r/I_b)$ can be adjusted in a binary manner, and since the value of adjustable reference impedance 48, $R_r$, is known, the desired value of element 42, $R_b$, can be digitized and stored in successive approximation register 55, and then telemetered to an external controller, such as telemetry controller 30 of FIG. 1.

As an alternative to adjusting $I_r$ by using binary input to first current generator 44 from successive approximation register 55, the value of adjustable reference impedance 48 can be adjusted through data bus 56. By varying the value of adjustable reference impedance 48, for example between $R_r$–$2R_r$, the desired result can still be achieved by feeding the output of comparator 50 to successive approximation register 55 until the value of $R_b$ is found and the resulting factor digitized and stored in successive approximation register 55 for telemetry of the body.

The primary advantage of the above-described invention lies in the use of a known reference impedance, such as adjustable reference impedance 48 having a resistance $R_r$, to measure the internal impedance of element 42 of a battery such as battery 40. This can be likened to using a voltage reference to measure an unknown voltage, however, no precise currents or voltages are required in the present invention. The only precise quantities necessary are $R_r$ and the ratio $(I_r/I_b)$.

It will be apparent that the above-described circuitry also has the advantage of providing an accurate end-of-life (EOL) signal without additions to the circuitry described above. It is only necessary to preselect a value of battery impedance, $R_b$, at which an EOL signal is desired. When this value of $R_b$ is telemetered to telemetry controller 30, it can be recognized in programmer 36 to set one or more EOL alarms.

Figure 3:
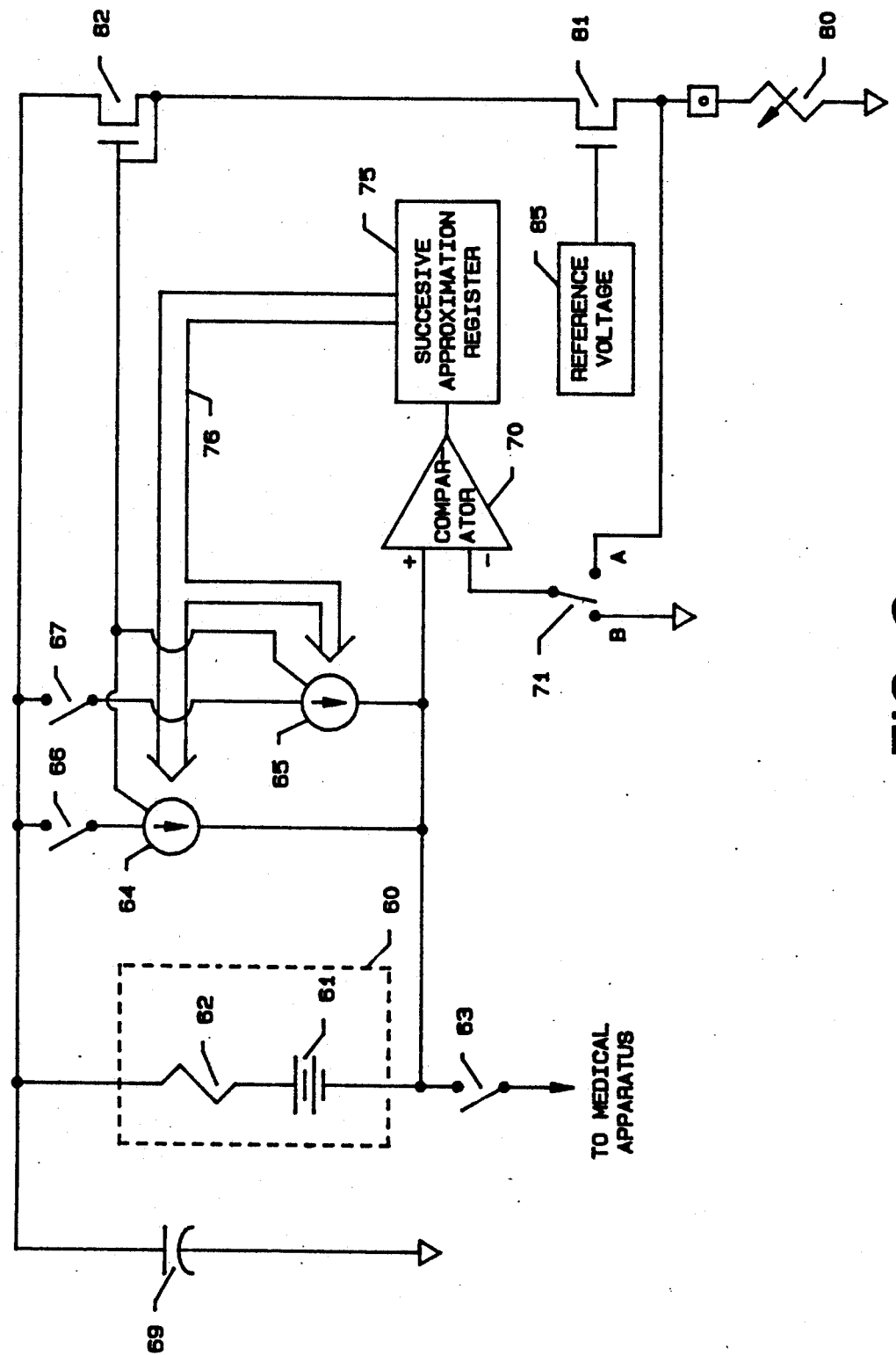

FIG. 3 is a schematic diagram of another preferred embodiment of this invention, disclosing a circuit intended to perform measurement of battery internal impedance, such as battery impedance measurement circuitry 21 of FIG. 1, and to provide a digitized signal representative of the value of the internal battery impedance and telemeter that signal to an external controller, such as telemetry controller 30 of FIG. 1.

A battery 60 is shown having an internal voltage 61, having a value $V_b$, and an internal impedance 62, having a value $R_b$. Battery 60 is connected to provide power to implanted medical apparatus (not shown) through a switch 63. Switch 63 can be selectively actuated to isolate battery 60 from the medical apparatus. A current generator 64 is connected across battery 60 through a switch 66. Another current generator 65 is connected across battery 60 through a switch 67. Current generators 64 and 65 are preferably digital-to-analog convertors, and may preferably be separate parts of the same digital-to-analog convertor.

The outputs of current generators 64 and 65 are connected to the positive input terminal of a comparator 70. The negative input terminal of comparator 70 is connected to a switch 71 that has terminals A and B. Terminal B of switch 71 is connected to ground. Terminal A of switch 71 is connected to a reference leg comprising a reference voltage 85 and an adjustable reference impedance 80 having a known value, $R_r$. The value, $V_r$, of reference voltage 85 is selected for convenience and is important only insofar as it determines a current level for the reference leg. Adjustable reference impedance 80 is preferably an external adjustable resistor. Adjustable reference impedance 80 is connected through a current source transistor 81 to reference voltage 85 and to input terminals on current generators 64 and 65, thus setting the value of the least significant bit of current generators 64 and 65. Adjustable reference impedance 80 is also connected across a capacitor 69 through current source transistors 81 and 82.

The output of comparator 70 is connected to the input of a successive approximation register 75. The output of successive approximation register 75 is connected through a data bus 76 to input terminals of current generators 64 and 65. Successive approximation register 75 is intended to be connected to telemetry circuitry such as telemetry send circuitry 27 of FIG. 1, for transmission to a controller such as telemetry controller 30 of FIG. 1.

In the operation of the circuit of FIG. 3, the first step is to automatically zero the system. Switch 63 is actuated to isolate battery 60 from the implanted medical apparatus, reference voltage 85 is turned on and current source transistors 81 and 82 thus turn on the reference leg. Next, switch 66 is closed to connect generator 64 across battery 60, thus driving a first current, $I_1$, and switch 71 is connected to its terminal B. Successive approximation register 75 is used to provide binary signals through data bus 76 to current generator 64, thus stepping up current $I_1$ until the comparator trips. Finally, switch 71 is moved to contact its terminal A, and switch 67 is closed to connect current generator 65 across battery 60, thus driving a second current $I_2$. Successive approximation register 75 is used to also provide binary signals through data bus 76 to current generator 65, thus stepping up current $I_2$ until the comparator again senses equality; this value of $I_2$ is saved.

As can be seen, $I_1$ simply accounts for the difference in voltage between an open circuit value of $V_b$ and the voltage on capacitor 69. Therefore:

$(I_2-I_1)/(V_r-0)$ (change in I)/(change in V)=$n/R_r$, where n=the binary value of $I_2$ or $R_b = R_r/n$ Thus, it can be seen that the preferred embodiment of FIG. 3 accomplishes the same purposes as described above for the embodiment of FIG. 2 by providing a factor indicative of the value of the internal impedance of an implanted battery, digitizing the factor and storing it as a binary number in a register for telemeter transfer to a device external to the body. Further, an EOL signal can be provided by the embodiment of FIG. 3 in the same manner as that described above for the embodiment of FIG. 2.

Note that the first current $I_1$ might alternately be zero, and the difference between the open circuit value of $V_b$ and the voltage on capacitor 69 could be stored on a capacitor in the comparator input circuit. Then the equation would be:

$(I_2-0)/V_R-0)$=(change in S) / (change in V) as before.

Having thus described the preferred embodiments of the present invention, those of skill in the art will readily appreciate the many other embodiments which can be employed within the scope of the claims hereto attached.

WE CLAIM:

1. In implantable electrical medical apparatus having telemetry means and battery means, battery impedance measurement apparatus comprising:
   a. means for selectively isolating said battery means from said medical apparatus;
   b. first circuit means selectively connectable in circuit with said battery means and including first current source means and reference impedance means;
   c. second circuit means selectively connectable in circuit with said battery means and including second current source means;
   d. control means for alternately connecting said first circuit means to said battery means for driving a first current and connecting said second circuit means to said battery means for driving a second current;
   e. measurement means for measuring the ratio of said first current to said second current; and,
   f. means connecting said measurement means to said telemetry means for transmission of said ratio.

2. The apparatus of claim 1 in which said measurement means includes:
   a. comparator means;
   b. register means;
   c. means connecting said first and said second circuit means to the input of said comparator means for providing said first and said second currents thereto;
   d. means connecting the output of said comparator means to the input of said register means; and,
   e. means connecting the output of said register means to said first circuit means for selectively varying said first current.

3. The apparatus of claim 2 in which said first and said second current source means comprise digital-to-analog converter means.

4. The apparatus of claim 2 in which said register means comprises successive approximation logic means.

5. The apparatus of claim 3 in which said register means comprises successive approximation logic means.

6. The apparatus of claim 1 in which said measurement means includes:
   a. comparator means;
   b. register means;
   c. means connecting said first and said second circuit means to the input of said comparator means for providing said first and said second currents thereto;
   d. means connecting the output of said comparator means to the input of said register means; and,
   e. means connecting the output of said register means to said first circuit means for selectively varying said reference impedance.

7. The apparatus of claim 6 in which said first and said second current source means comprise digital-to-analog converter means.

8. The apparatus of claim 6 in which said register means comprises successive approximation logic means.

9. The apparatus of claim 7 in which said register means comprises successive approximation logic means.

10. In implantable electrical medical apparatus having telemetry means and having battery means, battery impedance measurement apparatus comprising:
    a. means for electrically isolating said battery means from said medical apparatus;
    b. first current source means;
    c. means for selectively connecting said first current source means in circuit with said battery means to cause a first current;
    d. second current source means;
    e. means for selectively connecting said second current source means in circuit with said battery means to cause a second current;
    f. reference impedance circuit means;
    g. means for comparing said first and second currents;
    h. means connecting said reference impedance circuit means to said means for comparing for developing a signal from said first and second current indicative of the internal impedance of said battery means; and,
    i. means connecting said signal to said telemetry means.

11. The apparatus of claim 10 in which said means for comparing includes:
    a. comparator means;
    b. means selectively connecting said first and second current source means and said reference impedance means to the input of said comparator means;
    c. successive approximation register means; and,
    d. means connecting said register means between the output of said comparator means and said first and second current source means.

12. The apparatus of claim 11 in which said first and second current source means comprise digital-to-analog converter means.

13. In body implantable, battery powered medical apparatus having telemetry means, battery impedance measurement apparatus comprising:
    a. first adjustable current source means;
    b. second adjustable current source means;
    c. reference circuit means;
    d. comparator means having first and second input means and output means;
    e. current adjustment means connected between said comparator output means and said first and second current source means for adjusting said first and second current source means dependent on the output of said comparator means;
    f. first connection means for selectively disconnecting said battery means from said medical apparatus;
    g. second connection means for selectively connecting said first current source means in circuit with said battery means to provide a first current to said comparator means first input means, for connecting said comparator means second input means to circuit ground, and for connecting said current adjustment means to said first adjustable current source means; and,
    h. third connection means for selectively connecting said second current source means in circuit with said battery means to provide a second current to said comparator means first input means, for connecting said comparator means second input means to said reference circuit means, and for connecting said current adjustment means to said second adjustable current source means.

14. The apparatus of claim 13 in which:
    a. said first and second current source means comprise digital-to-analog converter means; and,
    b. said current adjustment means comprises successive approximation digital register means.

15. In implantable medical apparatus having telemetry means and battery means, battery impedance measurement apparatus comprising:
    a. means for isolating said battery means from said medical apparatus during an impedance measurement period;
    b. measurement means including reference circuit means having reference voltage means and reference impedance means;
    c. means for zeroing said measurement means including a first current generator selectively connected across said battery means and to said measurement means, and means for varying the output of said first generator means;
    d. means for developing and storing a signal indicative of the internal battery impedance of said battery means, including a second current generator selectively connected across said battery means and to said zeroed measurement means for comparison with said reference circuit means, and means for varying the output of said second generator means; and,
    e. means connecting said telemetry means to said measurement means for transmission of said stored signal.

16. The apparatus of claim 15 in which said measurement means includes:
    a. comparator means;
    b. successive approximation register means;
    c. means for alternately connecting said first and second current generator means to the input of said comparator means and alternately connecting circuit ground and said reference circuit means to the input of said comparator means;
    d. means connecting the input of said register means to the output of said comparator means; and,
    e. means alternately connecting the output of said register means to said first and second generator means for adjusting the current outputs thereof.

17. The apparatus of claim 16 in which said first and second current generators comprise digital-to-analog converters.

18. The apparatus of claim 16 in which said first and second current generators comprise separate parts of a single digital-to-analog converter.

* * * * *